(12) United States Patent
Ghelli et al.

(10) Patent No.: US 11,644,043 B2
(45) Date of Patent: May 9, 2023

(54) MAGNETIC LEVITATION CENTRIFUGAL PUMP

(71) Applicant: EUROSETS S.R.L., Medolla (IT)

(72) Inventors: Nicola Ghelli, Medolla (IT); Paolo Fontanili, Medolla (IT); Edgardo Costa Maianti, Medolla (IT)

(73) Assignee: EUROSETS S.R.L., Medolla (IT)

( * ) Notice: Subject to any disclaimer, the term of this patent is extended or adjusted under 35 U.S.C. 154(b) by 133 days.

(21) Appl. No.: 17/285,072

(22) PCT Filed: Oct. 16, 2019

(86) PCT No.: PCT/IB2019/058808
§ 371 (c)(1),
(2) Date: Apr. 13, 2021

(87) PCT Pub. No.: WO2020/079602
PCT Pub. Date: Apr. 23, 2020

(65) Prior Publication Data
US 2022/0025897 A1 Jan. 27, 2022

(30) Foreign Application Priority Data
Oct. 16, 2018 (IT) .......................... 102018000009506

(51) Int. Cl.
*F04D 29/048* (2006.01)
*F04D 29/22* (2006.01)
(Continued)

(52) U.S. Cl.
CPC ......... *F04D 29/048* (2013.01); *A61M 60/104* (2021.01); *A61M 60/232* (2021.01);
(Continued)

(58) Field of Classification Search
CPC .. F04D 13/024; F04D 13/025; F04D 13/0606; F04D 13/0626; F04D 13/0646;
(Continued)

(56) References Cited

U.S. PATENT DOCUMENTS 5,947,703 A * 9/1999 Nojiri ................... F04D 13/027
416/174
2020/0155740 A1 * 5/2020 Mori ................... A61M 60/232

FOREIGN PATENT DOCUMENTS

WO    WO93/20860 A1    10/1993
WO    WO-9320860 A1 *   10/1993 ............ A61M 1/101
WO    WO-9500185 A1 *   1/1995 ........... A61M 1/1036

* cited by examiner

*Primary Examiner* — Kenneth J Hansen
(74) *Attorney, Agent, or Firm* — Aslan Law, P.C.

(57) ABSTRACT

A magnetic levitation centrifugal pump, comprises: one hollow body provided with at least one inlet connector and with at least one outlet connector for blood; one rotor element, housed inside the hollow body and comprising at least one magnetic portion, where the rotor element can be commanded in rotation about an axis of rotation, without contact, by a stator element associable with the hollow body, the rotor element comprising at least one revolving body, which defines an upper surface supporting a plurality of blades which are adapted to convey blood towards the outlet connector; where the upper surface has a substantially concave shape and where the revolving body comprises at least one through hole which is positioned along the axis of rotation.

8 Claims, 3 Drawing Sheets

(51) Int. Cl.
*A61M 60/104* (2021.01)
*A61M 60/422* (2021.01)
*A61M 60/804* (2021.01)
*A61M 60/232* (2021.01)

(52) U.S. Cl.
CPC ........ *A61M 60/422* (2021.01); *A61M 60/804* (2021.01); *F04D 29/2216* (2013.01)

(58) Field of Classification Search
CPC .............. F04D 29/426; F04D 49/4293; F04D 29/2211; F04D 29/2216; F04D 29/2238; A61M 60/104; A61M 60/221; A61M 60/226; A61M 60/232; A61M 60/81; A61M 60/804; A61M 60/806; A61M 60/808
See application file for complete search history.

MAGNETIC LEVITATION CENTRIFUGAL PUMP

CROSS-REFERENCE TO RELATED APPLICATIONS

This application claims priority to IT Patent Application No. 102018000009506 filed on Oct. 16, 2018, and this application claims priority to and is a 371 of international PCT Application No. PCT/IB2019/058808 filed on Oct. 16, 2019, the entire contents of which are hereby incorporated by reference.

TECHNICAL FIELD

The present invention relates to a magnetic levitation centrifugal pump.

BACKGROUND ART

The magnetic levitation centrifugal pumps used in the biomedical sector are generally composed of an internally hollow body, provided with at least one blood inlet connector and one blood outlet connector, inside which is housed a rotor element provided with a plurality of blades adapted to convey, as a result of the rotation of the rotor element itself, the incoming blood towards the outlet connector.

The rotor element comprises a portion of magnetic material, and outside the hollow body a stator element is positioned which is adapted to define at least one magnetic field for lifting and controlling the rotor element in rotation inside the hollow body.

Moreover, the rotor element comprises a revolving body on which a plurality of blades is arranged in a radial pattern.

The blades mentioned above are positioned on the upper portion of the rotor element facing the inlet connector, which has a truncated-cone shape.

The inclined surface of the upper portion of the rotor element is intended to accompany the entry of blood into the hollow body.

These centrifugal pumps of known type do have some drawbacks.

In particular, the blood entering the hollow body, as a result of the impact with the upper portion of the rotor element, is likely to be damaged.

Another drawback consists in the fact that the impact of blood with the inclined surface of the rotor element can lead to the formation of air bubbles, which must then be removed before the reintroduction of the blood itself into the patient.

Some types of centrifugal pumps are known from WO 93/20860 A1 and from CN 107693868 A, which, due to their conformation do not allow to avoid blood stagnation inside the relevant hollow body and do not allow optimizing the ratio between the head of the pump and the turbulence inside it.

DESCRIPTION OF THE INVENTION

The main aim of the present invention is to devise a magnetic levitation centrifugal pump which allows reducing the damage of the blood due to its interaction with the rotor element.

Within this aim, one object of the present invention is to reduce the formation of air bubbles inside the pump itself.

Another object of the present invention is to avoid blood stagnation inside the relevant hollow body.

Yet another object is to optimize the ratio between the head of the pump and the turbulence inside it.

Another object of the present invention is to devise a magnetic levitation centrifugal pump which allows overcoming the aforementioned drawbacks of the prior art in the ambit of a simple, rational, easy, effective to use and low cost solution.

The aforementioned objects are achieved by the present magnetic levitation centrifugal pump having the characteristics of claim 1.

BRIEF DESCRIPTION OF THE DRAWINGS

Other characteristics and advantages of the present invention will be more evident from the description of a preferred, but not exclusive, embodiment of a magnetic levitation centrifugal pump, illustrated by way of a non-limiting example in the accompanying tables of drawing in which.

EMBODIMENTS OF THE INVENTION

Figure 1:
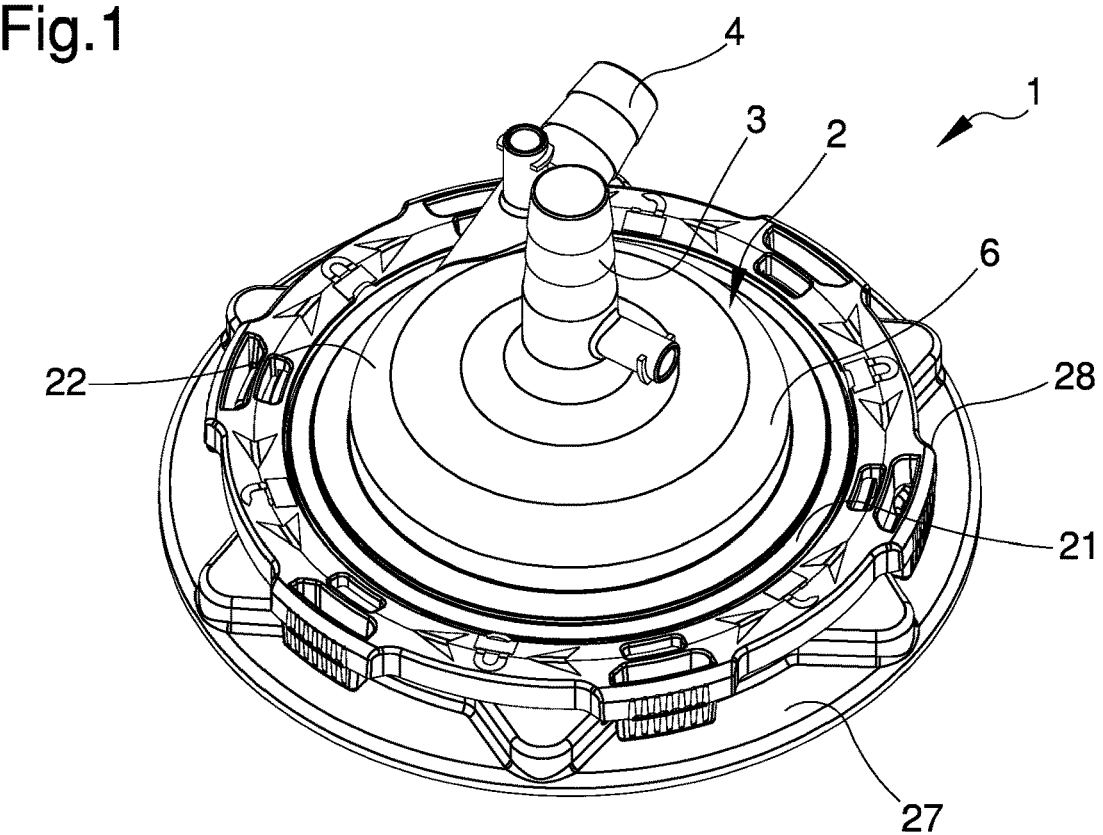
FIG. 1 is an axonometric view of a magnetic levitation centrifugal pump according to the invention.
Figure 2:
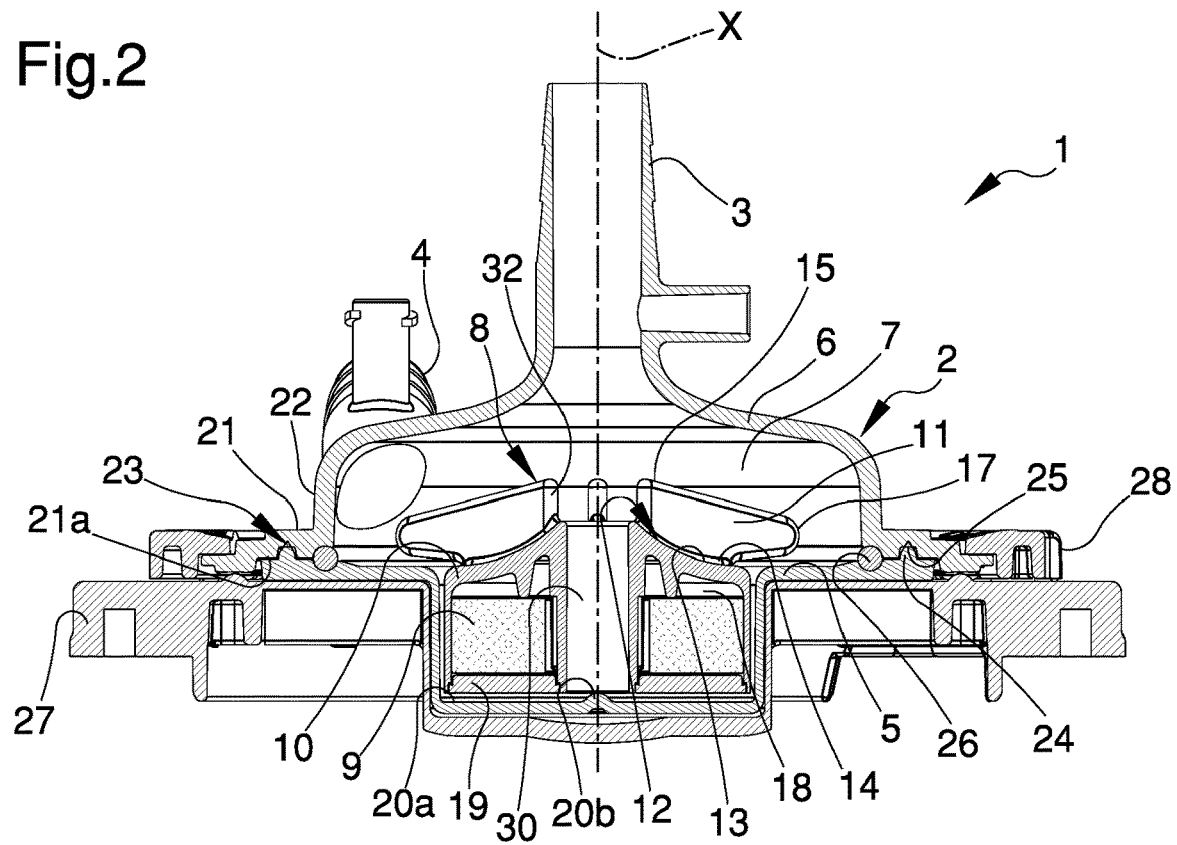
FIG. 2 is a cross-sectional view of the pump in FIG. 1.
Figure 3:
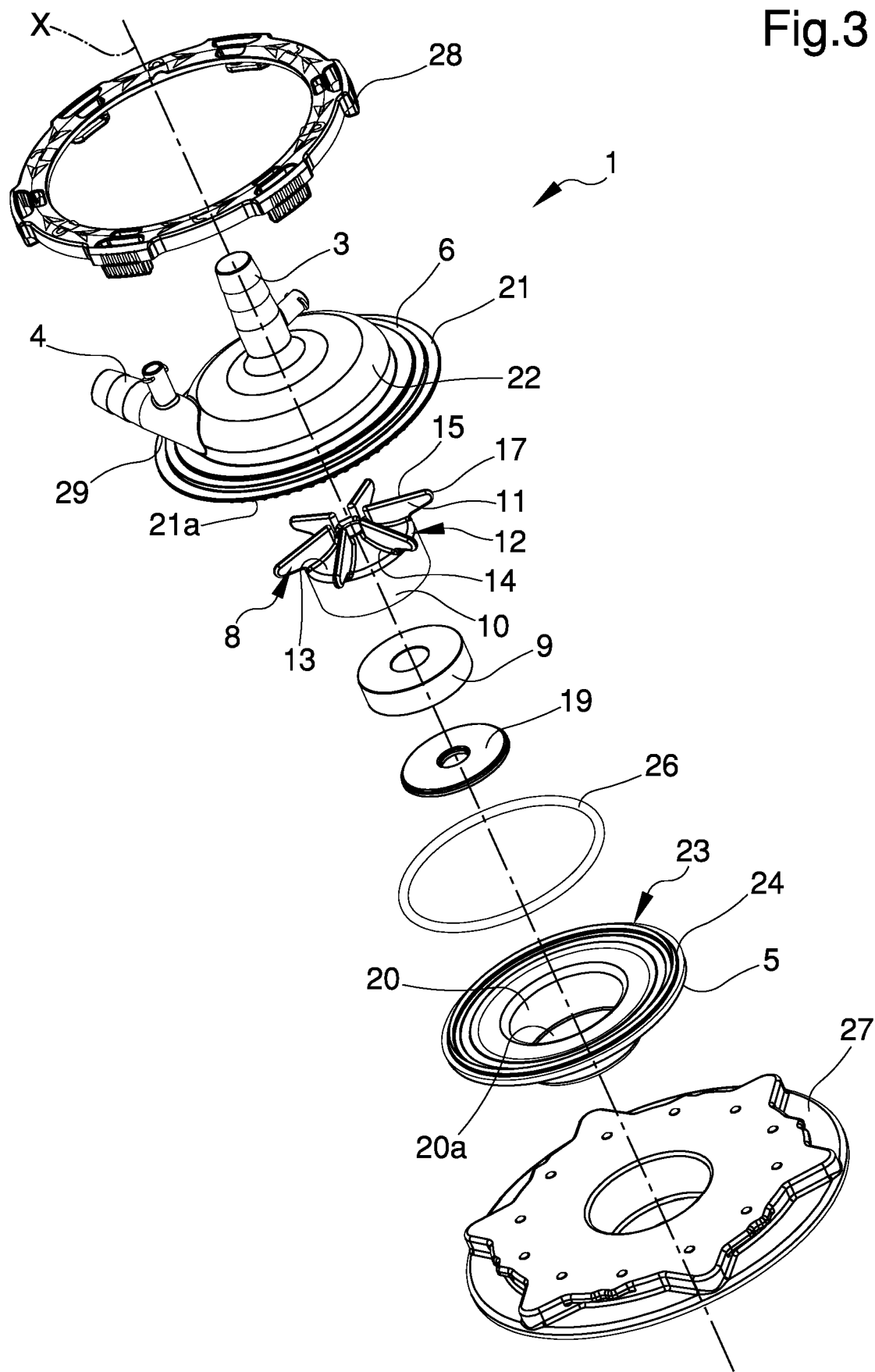
FIG. 3 is an exploded view of the pump in FIG. 1.
Figure 4:
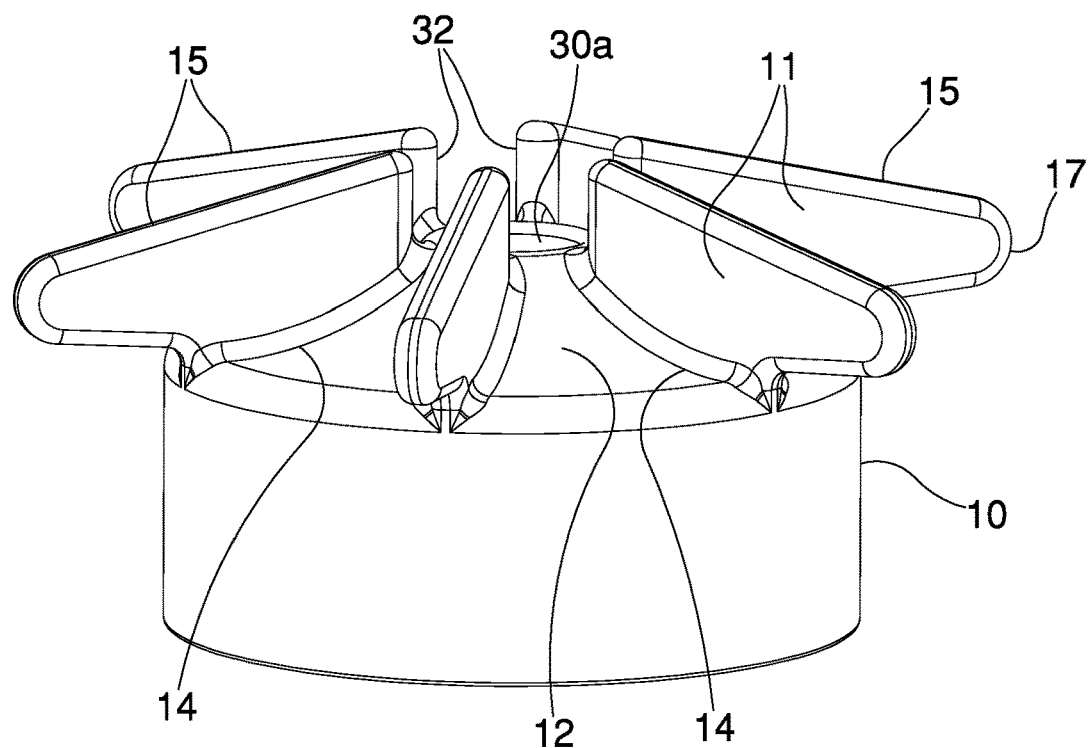
FIG. 4 is an axonometric view of the revolving body of the pump in FIG. 1.
Figure 5:
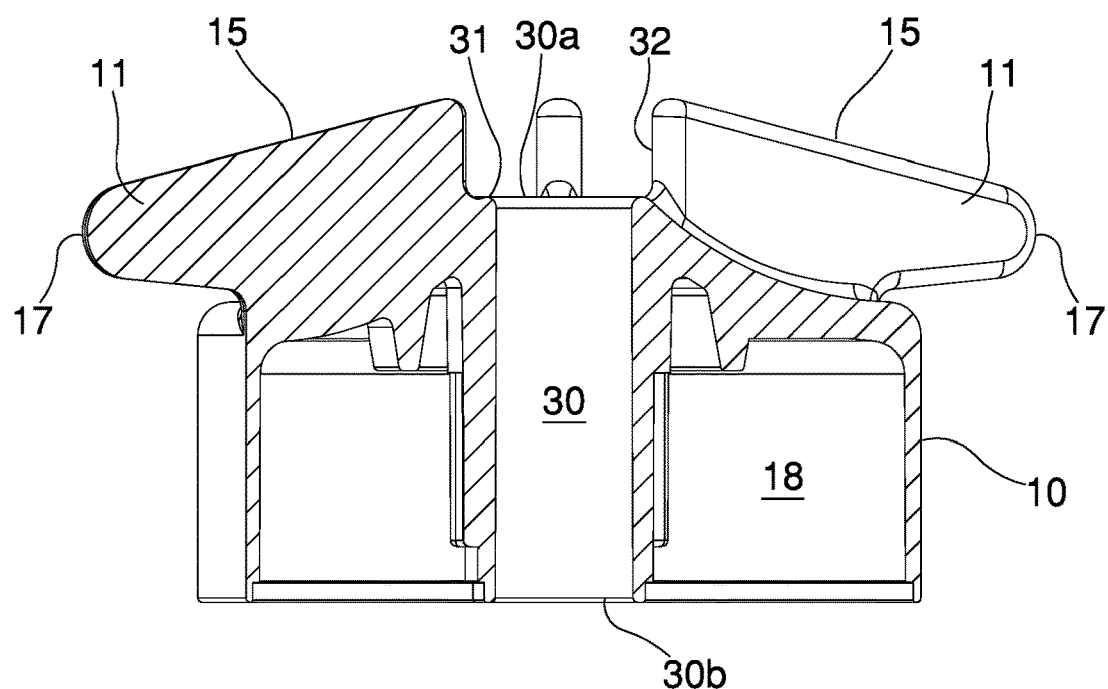
FIG. 5 is a cross-sectional view of the revolving body in FIG. 4.

With particular reference to these illustrations, reference numeral 1 globally indicates a magnetic levitation centrifugal pump.

The pump 1 comprises at least one hollow body 2 provided with at least one inlet connector 3 for the venous blood coming from a patient and with at least one outlet connector 4 for the venous blood to be conveyed to a blood oxygenation device.

The hollow body 2 therefore defines a volume 7, on which the inlet connector 3 and the outlet connector 4 face, inside which is housed at least one rotor element 8, comprising at least one magnetic portion 9.

The rotor element 8 can be commanded in rotation about an axis of rotation X, without contact, by a stator element (not shown in the illustrations), associable with the hollow body 2. More in detail, the rotor element 8 is commanded in rotation directly from the stator, i.e. without the interposition of additional intermediate elements.

The way in which the rotation of the rotor element 8 is controlled, although not related to in the present invention, is widely known to the technician in the field.

In particular, the stator element comprises a plurality of windings intended to be crossed by the electric current for the formation of one or more magnetic fields which are adapted to interact with the rotor element 8 to raise and bring it in rotation around the axis of rotation X.

More specifically, the rotor element 8 comprises at least one revolving body 10, which defines an upper surface 12 supporting a plurality of blades 11 which are adapted to convey the blood entering the volume 7 towards the outlet connector 4.

The blades 11 are appropriately arranged on the upper surface 12 in a radial pattern.

According to the invention, the upper surface 12 has a substantially concave shape and the revolving body 10 has a through hole 30 which is positioned along the axis of rotation X.

In particular, the venous blood entering the volume 7 through the inlet connector 3 meets the blades 11 and, while one part passes through the hole 30, the other part contacts the upper surface 12 and, due to the rotation of the blades 11, is conveyed towards the outlet connector 4.

Advantageously, the upper surface 12 has a curvilinear extension to define a saddle 13 adapted to receive the blood entering the inlet connector 3.

One part of the blood entering the volume 7 internally therefore contacts the upper surface 12, the curvilinear shape of which accompanies the descent thereof, preventing it from being thrown out of the rotor element 8 as a result of the impact, thus reducing the risk of damage to the blood itself.

The hole 30 thus allows the recirculation of the part of the blood entering the volume 7, thus avoiding blood stagnation phenomena.

More particularly, the hole 30 has a first opening 30*a* facing the upper surface 12.

Appropriately, the upper surface 12 has a joining profile 31 with the first opening 30*a*.

The hole 30 then has a second opening 30*b*, opposite the first opening 30*a*, which faces a bottom wall 20*a* of the hollow body 2.

Conveniently, the blades 11 have a coupling profile 14 for coupling to the upper surface 12, which profile also has a substantially curvilinear extension, so as to join with the upper surface itself and facilitate the flow of blood.

Preferably, the blades 11 have an upper profile 15, opposite the coupling profile 14, having a substantially rectilinear extension (i.e. except for the machining tolerances).

Advantageously, the blades 11 have a joining profile 17 of the coupling profile 14 with the upper profile 15, where the joining profile 17 protrudes from the overall dimensions of the revolving body 10. The term "overall dimensions" of the revolving body 10 means the extension of the revolving body 10 transverse to the axis of rotation X.

The joining profile 17 protrudes from the overall dimensions of the revolving body 10 in order to define a large surface area of impact with the blood. In the preferred embodiment shown in the figures, the joining profile 17 has a curvilinear extension.

The blades 11 do also have a rear profile 32, positioned between the coupling profile 14 and the upper profile 15 having a substantially rectilinear extension (i.e. except for the machining tolerances and the ends connected to the adjacent profiles).

Advantageously, the rear profile 32 extends parallel to the axis of rotation X.

The shape of the rear profile 32 allows dividing the flow of blood entering the volume 7 into two parts, one of which is conveyed into the hole 30 and the other is conveyed along the upper wall 12.

The rear profile 32 is located on the opposite side of the joining profile 17 of the relevant blade 11.

The rear profiles 32 of the blades 11 are then positioned in a radial pattern around the first opening 30*a* of the hole 30.

The revolving body 10 is provided with a housing seat 18, defined at the bottom portion, inside which is inserted the magnetic portion 9, which is closed below by a retaining element 19.

The magnetic portion 9 is arranged around the hole 30.

The hollow body 2 comprises at least one lower element 5 and at least one upper element 6 separated from each other and mutually coupled.

Additionally, the lower element 5 has a containment seat 20 adapted to accommodate at least one portion of the revolving body 10, which defines the bottom wall 20*a*. The bottom wall 20*a* is provided with a guiding member 20*b*, defined at the axis of rotation X, for the centering of the rotor element 8.

Advantageously, the upper element 6 has at least one perimeter flange 21 for coupling to the lower element 5 and at least one substantially dome-shaped body 22, which protrudes from the perimeter flange 21, where the outlet connector 4 is associated with the dome-shaped body 22.

Preferably, the perimeter flange 21 defines a coupling surface 21*a* with the lower element 5 and the outlet connector 4 is raised with respect to the coupling surface 21*a*.

In the embodiment shown in the illustrations, the coupling surface 21*a* is substantially flat.

Between the outlet connector 4 and the perimeter flange 21, an air space 29 is defined inside which the tightening means can be inserted to tighten the upper element 6 and the lower element 5 during the welding operations.

Appropriately, sealing means 26 are positioned between the coupling surface 21*a* and the lower element 5.

Advantageously, the inlet connector 3 and the outlet connector 4 are substantially elongated in shape.

In the particular embodiment shown in the illustrations, the inlet connector 3 is positioned at the top of the upper element 6 and extends coaxially to the axis of rotation X.

Conveniently, the upper element 6 and the lower element 5 are provided with relevant centering means 23 adapted to ensure their correct mutual positioning.

More in detail, the centering means 23 comprise at least one relief 24 defined on one of either the coupling surface 21*a* or the lower element 5 and at least one recess 25 defined on the other of either the lower element 5 or the coupling surface 21*a*, where the relief 24 is adapted to be inserted in the recess 25 following the positioning of the upper element 6 on the lower element 5.

In the particular embodiment shown in the illustrations, the upper element 6 and the lower element 5 have a substantially circular section, therefore the recess 25 and the relief 24 have a substantially annular extension.

The attached figures also show, although not part of the present invention, the covering element 27 of the stator element mentioned above, which is intended to support the hollow body 2, and the anchoring element 28 of the hollow body 2 to the covering element 27.

It has in practice been found that the described invention achieves the intended objects and, in particular, the fact is underlined that the substantially concave shape of the upper surface allows reducing the risk of damage that the blood may suffer as a result of the impact with the revolving body.

In addition, the presence of the saddle means that the trajectory run by the blood is linear, thus reducing the formation of air bubbles inside it compared to the pumps of known type.

The invention claimed is:

1. A magnetic levitation centrifugal pump comprising:
   at least one hollow body provided with at least one inlet connector and with at least one outlet connector for blood; and
   at least one rotor element, housed inside said at least one hollow body and comprising at least one magnetic portion, where said at least one rotor element can be commanded in rotation about an axis of rotation, without contact, by a stator element associable with said at least one hollow body, said at least one rotor element comprising at least one revolving body, which defines an upper surface supporting a plurality of blades which are adapted to convey blood towards said at least one outlet connector, wherein said upper surface has a substantially concave shape and said at least one revolving body comprises at least one through hole which is positioned along said axis of rotation, said upper surface has a curvilinear extension to define a saddle which is adapted to receive the blood entering said at least one inlet connector, said at least one hole has a first opening facing said upper surface, said upper surface has a joining profile with said first opening, said at least one hollow body has a bottom wall, said at least one hole has a second opening, opposite said first opening which faces said bottom wall, said plurality of blades have a coupling profile to said upper surface, having a substantially curvilinear extension, said plurality of blades have an upper profile, opposite said coupling profile, having a substantially rectilinear extension, said plurality of blades have a joining profile of said coupling profile to said upper profile, where said joining profile protrudes with respect to the overall dimensions of said at least one revolving body, and said joining profile has a curvilinear extension.

2. The magnetic levitation centrifugal pump according to claim 1, wherein said plurality of blades have a rear profile positioned between said coupling profile and said upper profile having a substantially rectilinear extension so as to divide the blood entering said at least one hollow body.

3. The magnetic levitation centrifugal pump according to claim 2, wherein said rear profile extends substantially parallel to said axis of rotation.

4. The magnetic levitation centrifugal pump according to claim 3, wherein said rear profiles of said plurality of blades are positioned in a radial pattern around said first opening.

5. The magnetic levitation centrifugal pump according to claim 4, wherein said rear profile is opposite said joining profile.

6. The magnetic levitation centrifugal pump according to claim 2, wherein said rear profiles of said plurality of blades are positioned in a radial pattern around said first opening.

7. The magnetic levitation centrifugal pump according to claim 2, wherein said rear profile is opposite said joining profile.

8. The magnetic levitation centrifugal pump according to claim 3, wherein said rear profile is opposite said joining profile.

* * * * *